US006194599B1

United States Patent
Miller et al.

(10) Patent No.: US 6,194,599 B1
(45) Date of Patent: Feb. 27, 2001

(54) PROCESS FOR PREPARING BIARYL COMPOUNDS

(75) Inventors: Joseph A. Miller, San Jose; Robert P. Farrell, San Francisco, both of CA (US)

(73) Assignee: Catalytica, Inc., Mountain View, CA (US)

( * ) Notice: Subject to any disclaimer, the term of this patent is extended or adjusted under 35 U.S.C. 154(b) by 0 days.

(21) Appl. No.: 08/825,792

(22) Filed: Apr. 8, 1997

(51) Int. Cl.⁷ .............................. C07C 253/30; C07C 2/84; C07D 207/30; C07D 307/34; C07D 333/04
(52) U.S. Cl. ....................... 558/411; 546/311; 546/348; 548/560; 549/80; 549/506; 560/102; 568/323; 585/25
(58) Field of Search ........................ 546/311; 549/80; 558/378, 411; 560/102; 568/323; 585/25

(56) References Cited

U.S. PATENT DOCUMENTS

| | | | |
|---|---|---|---|
| 4,263,466 | 4/1981 | Colon et al. | 585/421 |
| 4,620,025 | * 10/1986 | Sletzinger et al. | 560/102 X |
| 4,912,276 | 3/1990 | Puckette | 585/425 |
| 4,990,647 | * 2/1991 | Himmler et al. | 560/102 X |
| 5,128,355 | 7/1992 | Carini et al. | 514/381 |
| 5,130,439 | 7/1992 | Lo et al. | 548/110 |
| 5,237,116 | * 8/1993 | Corley | 549/80 X |
| 5,288,895 | 2/1994 | Bousset et al. | 558/378 |
| 5,364,943 | 11/1994 | Rosen et al. | 546/223 |
| 5,559,277 | 9/1996 | Beller et al. | 585/469 |

FOREIGN PATENT DOCUMENTS

| | | | |
|---|---|---|---|
| 0470794A1 | 8/1991 | (EP) | C07C/255/50 |
| 0470795A1 | 8/1991 | (EP) | C07C/255/50 |
| 08231454 | 9/1996 | (JP) . | |

OTHER PUBLICATIONS

Sainsbury, "Modern Methods of Aryl–Aryl Bond Formation", Tetrahedron Report No. 98, Tetrahedron vol. 36, 1980, 3327 to 3359.

Bringmann et al., "The Directed Synthesis of Biaryl Compounds: Modern Concepts and Strategies", Angew, Chem, Int. Ed. Engl., vol. 29, (1990), 977–991.

Meyers et al., "Nucleophilic Aromatic Substitution on o–(Methoxy)aryloxazolines. A Convenient Synthesis of o–Alkyl–, o–Alkylidene–, and o–Arylbenzoic Acids", J. Org. Chem. vol. 43 (1978), pp. 1372–1379.

Carini et al., "Nonpeptide Angiotensin II Receptor Antagonists: The Discovery of a Series of N–(Biphenylmethyl)imidazoles as Potent, Orally Active Antihypertensives", J. Med, Chem., vol. 34 (1991), 2525–2547.

Tamao et al., "Nickel–Phosphine Complex–Catalyzed Grignard Coupling. I. Cross–Coupling of Alkyl, Aryl, and Alkenyl Grignard Reagents with Aryl and Alkenyl Halides: General Scope and Limitations", Bull. Chem. Soc. Japan, vol. 49 (1976), pp. 1958–1969.

Grushin et al., "Transformations of Chloroarenes, Catalyzed by Transition–Metal Complexes", Chem. Rev., vol. 94 (1994), pp. 1047–1062.

Clough et al., "Coupling of Nonequivalent Aromatic Rings by Soluble Nickel Catalysts. A General Route to the 1,8–Diarylnaphthalenes1a", J. Org. Chem., vol. 41 (1976), pp. 2252–2255.

Pridgen et al, "Oxazolines. 3. Regioselective Synthesis of 2–(Monosubstituted phenyl) and/or Unsymmetrically 2–(Disubstituted phenyl) 2–Oxazolines by Cross–Coupling Grignard Reagents to (Haloaryl)–2–oxazolines", J. Org. Chem., vol. 47 (1982), pp. 4319–4323.

Negishi et al., "Selective Carbon–Carbon Bond Formation via Transition Metal Catalysis. 3. A Highly Selective Synthesis of Unsymmetrical Biaryls and Diarylmethanes by the Nickel– or Palladium–Catalyzed Reaction of Aryl– and Benzylzine Derivatives with Aryl Halides", J. Org. Chem. vol. 42 (1977), pp. 1821–1823.

Zhu et al., "The Direct Formation of Funtionalized Alkyl(aryl)zinc Halides by Oxidative Addition of Highly Reactive Zinc with Organic Halides and Their Reactions with Acid Chlorides, α,β–Unsaturated Ketones, and Allylic, Aryl, and Vinyl Halides", J. Org. Chem. vol. 56 (1991), pp. 1445–1453.

Silbille et al., "Electrochemical Conversion of Funtionalised Aryl Chlorides and Bromides to Arylzinc Species", J. Chem. Soc. Chem. Comm., 1992, pp. 283–284.

Mantlo et al., "Potent, Orally Active Imidazo[4,5–b]pyridine–Based Angiotensin II Receptor Antagonists", J. Med. Chem., vol. 34 (1991), pp. 2919–2922.

Percec et al., "Aryl Mesylates in Metal Catalyzed Homo– and Cross–Coupling Reactions. 4. Scope and Limitations of Aryl Mesylates in Nickel Catalyzed Cross–Coupling Reactions", J. Org. Chem. 1995, 60, 6895–6903.

Zembayashi et al., "Nickel–Phosphine Complex–Catalyzed Homo Coupling of Aryl Halides in the Presence of Zinc Powder", Tetrahedron Letters No. 47, (1977) pp. 4089–4092.

Colon et al., "Coupling of Aryl Chlorides by Nickel and Reducing Metals", J. Org. Chem., vol. 51 (1986), pp. 2627–2637.

(List continued on next page.)

Primary Examiner—Michael G. Ambrose
(74) Attorney, Agent, or Firm—Al A. Iecminek; John H. Grate

(57) ABSTRACT

The present invention provides a process for preparing biaryl compounds comprising reacting an arylzinc reagent with an arylchloride in the presence of a nickel catalyst or a palladium catalyst. The present invention specifically provides a process for the preparation of 2-(4'-methylphenyl)benzonitrile comprising reacting a 4-methylphenylzinc reagent with 2-chlorobenzonitrile in the presence of a nickel catalyst or a palladium catalyst.

20 Claims, No Drawings

OTHER PUBLICATIONS

Kageyama et al., "Nickel–Catalyzed Cross–Coupling Reaction of Aryl Halides in Pyridine. A Practical Synthesis of 4'–Methylbiphenyl–2–carbonitrile As a Key Intermediate of Angiotensine II Receptor Antagonists", Synlett, 1994, pp. 371–372.

Miyaura et al, "The Palladium–Catalyzed Cross–Coupling Reaction of Phenylboronic Acid with Haloarenes in the Presence of Bases", Synthetic Communications vol. 11 (1981), 513.

Ali et al., "Palladium–Catalysed Cross–Coupling Reactions of Arylboronic Acids with π–Deficient Heteroaryl Chlorides", Tetrahedron, vol. 48 (1992), pp. 8117–8126.

Saito et al., "A Synthesis of Biaryls via Nickel(O)–Catalyzed Cross–Couplling Reaction of Chloroarenes with Phenylboronic Acids", Tetrahedron Letters, vol. 37 (1996), pp. 2993–2996.

Kalinin et al., "Carbon–Carbon Bond Formation in Heterocycles Using Ni– and Pd–Catalyzed Reactions", Synthesis, 1992, 413–432.

Voegtle et al., "Tweezer–shaped hydrocarbons", Chemical Abstracts No. 118:6716, vol. 125 (1992), pp. 219–235.

House et al., "Reactions of the 1,8–Dipenylanthracene System", J. Org. Chem., vol. 45 (1980), pp. 1807–1817.

House et al., "Unsummetrically Substituted 1,8–Diarlanthracenes", J. Org. Chem. vol. 51 (1986), pp. 921–929.

House et al., "Unsymmetrically Substituted 2,7–Dimethyl–1,8–diarylanthracenes", J. Org. Chem. vol. 58 (1993), pp. 7516–1523.

* cited by examiner

PROCESS FOR PREPARING BIARYL COMPOUNDS

FIELD OF THE INVENTION

This invention relates generally to preparing biaryl compounds by arylaryl coupling reactions. More specifically, it relates to preparing biaryl compounds by reacting an aryl-metal reagent with an aryl halide. It further relates to preparing biaryl compounds by reacting an arylmetal reagent with an arylchloride and to preparing biaryl compounds by reacting an arylzinc reagent with an aryl halide. Biaryl compounds are valuable as fine chemicals for liquid crystals and related applications and as precursors to pharmaceutically active compounds. In particular, 2-(4'-methylphenyl)benzonitrile (also known as 4-methyl-2'-cyanobiphenyl) can be used as an intermediate in the preparation of various angiotensin II antagonists.

BACKGROUND OF THE INVENTION

The following references give reviews of methods of preparing biaryl compounds: Sainsbury, *Tetrahedron,* vol. 36 (1980), pp. 3327–3359 and Bringman et al., *Angew. Chem. Int. Ed. Engl.,* vol. 29, (1990), 977–991.

In the Meyers oxazoline method to make unsymmetrical biaryl 2-carboxylic acid derivatives, disclosed in Meyers et al, *J. Org. Chem.,* vol. 43 (1978), pp. 1372–1379, the carboxyl group in 2-methoxybenzoic acids is converted into an oxazoline to activate the 2-methoxy group for nucleophilic substitution by arylmagnesium halide or aryllithium reagent and to protect the carboxyl group in a form that is not subject to nucleophilic attack by the aryl carbanion species.

Carini et al., *J. Med. Chem.,* vol. 34 (1991), 2525–2547 disclose the application of the Meyers oxazoline method to the preparation of 2-(4'-methylphenyl)benzonitrile by the following steps: 1) 2-methoxybenzoic acid is reacted with thionyl chloride; 2) the acyl chloride formed is treated with 2-amino-2-methyl-1-propanol, which provides an amide in the crude form; 3) this amide is subjected to the action of thionyl chloride, forming 4,4-dimethyl-2-(2-methoxyphenyl)-oxazoline (yield 88% from the acid chloride); 4) this oxazoline derivative is reacted with p-tolyl-magnesium bromide and the complex formed is hydrolyzed, which gives 4,4-dimethyl-2-(4'-methylbiphenyl-2'-yl)-oxazoline (yield 91%); and 5) the oxazoline derivative formed is then treated with phosphorus oxychloride, which finally provides 2-(4'-methylphenyl)benzonitrile (yield 96%). The overall yield is 77% but this process has the disadvantage of requiring the use of 5 steps, starting from commercially available products, due to the prior formation of the dimethyloxazolinyl group and its subsequent conversion to the cyano group. U.S. Pat. No. 5,128,355 (to Carini et al.) similarly exemplifies the application of the multistep Meyers oxazoline method to the preparation of 2-(4'-methylphenyl)benzoic acid (example 85), and the conversion of this benzoic acid to the benzonitrile Example 89). Implicitly, these references illustrate that when an aryl magnesium reagent (in this case, p-tolyl magnesium bromide) is used directly to provide the aryl group in an arylbenzonitrile (in this case, 2-(4'-methyl-phenyl) benzonitrile) the nitrile group cannot be present in the substrate that is treated with the aryl magnesium reagent. It must be in a protected precursor form during the coupling process (in this case, as the dimethyloxazolinyl group).

Tamao et al., *Bull. Chem. Soc. Japan,* vol. 49 (1976), pp. 1958–1969, discloses that arylbromides can be reacted with arylmagnesium halides (aryl Grignard reagents) in the presence of dihalodiphophinenickel complexes to give biaryl compounds. A sole disclosed attempt to react an aryl chloride (chlorobenzene) with an arylmagnesium halide (mesityl) was reported to give only a 6% yield of the desired biaryl. Similar reactions of the bromobenzene with mesityl-magnesium bromide gave yields of 78–96%. This reference states, "The most serious limitation is that the substituents on the organic halides and on the Grignard reagents are restricted to those which cannot react with Grignard reagents."

In a review article titled "Transformations of Chloroarenes, Catalyzed by Transition-Metal Complexes", *Chem. Rev.,* vol 94 (1994), pp. 1047–1062, Grushin et al. state, "Unfortunately, the most reactive iodo- and bromoarenes are the most expensive ones, whereas aryl fluorides are both costly and unreactive. Chloroarenes are certainly the most attractive aryl halides for synthetic applications on an industrial scale, because they are inexpensive and readily available in bulk quantities. The main drawback here is the exceedingly high stability of the aromatic carbon-chlorine bond whose inertness remains the major obstacle on the way to wide utilization of chloroarenes."

Clough et al., *J. Org. Chem.,* vol. 41 (1976), pp. 2252–2255 discloses that 1,8-dihalonapthalenes can be reacted with arylmagnesium halides in the presence of certain soluble nickel catalysts to give 1,8-diarylnaphthalenes. The reactivities of the 1,8-dihalonaphthalenes in this system was found to be I>Br>>Cl.

U.S. Pat. No. 4,912,276 discloses that aryl chlorides can be reacted with arylmagnesium halides in the presence of a nickel-triorganophosphine catalyst to give biaryl compounds. The disclosed scope of the aryl groups in the arylchlorides, the arylmagnesium reagents, and the biaryl compounds consists of phenyl and substituted phenyl with hydrocarbyl or hydrocarbyloxy substituents or protected carbonyl-containing derivatives thereof. These are all substituents that are unreactive to arylmagnesium halides. The only biaryl whose preparation is exemplified by working examples is the symmetrical biaryl 2,2'dimethylbiphenyl, prepared from 2-chlorotoluene and o-tolylmagnesium chloride (derived from 2-chlorotoluene).

Pridgen, *J. Org. Chem.,* vol. 47 (1982), pp. 4319–4323 discloses two examples in which 2-(chlorophenyl)-2-oxazolines are reacted with arylmagnesium halides in the presence of a diphosphine-chelated nickel catalyst to give the corresponding 2-(biaryl)-2-oxazoline compounds. The oxazoline group activates the aryl chloride and provides a form of the carboxyl group that is protected from reaction with the arylmagnesium halide.

U.S. Pat. No. 5,288,895 discloses a process for the preparation of 4-methyl-2'-cyanobiphenyl (a.k.a. 2-(4'-methylphenyl)benzonitrile) wherein a 2-halobenzonitrile is reacted with a 4-methylphenyl magnesium halide in the presence of manganous salt. The Examples of this patent, which describe reactions of 2-chlorobenzonitrile, report analyzed chemical yields of 60–75% of 2-(4'-methylphenyl) benzonitrile) in a recovered "brown viscous liquid". Recrystallizations (plural) give the product as a beige solid, but the yields of these purified solids are not reported.

This patent also discloses tests showing that the direct reaction of 4-methylphenyl magnesium bromide with 2-chlorobenzonitrile, in the absence of manganese salt, "proves incapable of giving 4-methyl-2'-cyanobiphenyl". Analysis showed unreacted 2-chlorobenzonitrile and the addition product of the reagent to the nitrile group, 2-chloro-1-phenyl(4-tolyl)ketone, but no trace of 2-(4'-methylphenyl) benzonitrile.

This patent also discloses attempted reactions of several equivalents of 4-methylphenyl magnesium bromide with 1 equivalent of 2-bromobenzonitrile and 0.3 equivalents of either $PdCl_2$ or $NiCl_2$ in tetrahydrofuran at 0° C. Yields of 22% and 27%, respectively, of 2-(4'-methylphenyl) benzonitrile were analyzed in recovered crude residue. Similar reactions with 0.003 equivalents tetrakis(triphenylphosphine)palladium(0) at 0 and 65° C. gave only a 1% yield in the residue.

Negishi et al, *J. Org. Chem.*, vol. 42 (1977), pp. 1821–1823 discloses reactions of arylzinc derivatives (arylzinc chloride or diarylzinc) with aryl bromides or iodides in the presence of nickel or palladium complexes as catalysts to produce unsymmetrical biaryls. The arylzinc derivatives were prepared by a metathesis reaction between the corresponding aryllithium and zinc dichloride. The reference does not report any attempt to react an arylzinc derivative with an aryl chloride and is silent as to whether aryl chlorides are suitable or unsuitable as alternatives to the aryl bromides or iodides. The authors comment on the ability of arylzinc derivatives to tolerate various electrophilic functional groups, such as nitrile and ester, in the arylbromide or iodide.

Zhu et al., *J. Org. Chem.*, vol. 56 (1991), pp. 1445–1453 similarly discloses reactions of arylzinc halides with aryl bromides or aryl iodides in the presence of a palladium tetrakis(triphenylphosphine as catalyst to form biaryl compounds. The arylzinc halides were prepared by the reaction of the arylhalide with a form of highly reactive zinc.

Silbille et al., *J. Chem. Soc. Chem. Comm.*, 1992, pp. 283–284 discloses a reaction of 4-trifluoromethylphenylzinc chloride, prepared from 4-trifluoromethylchlorobenzene, with 4-bromobenzonitrile using the palladium complex $PdCl_2(PPh_3)_2$ as catalyst to form 4-trifluoromethylphenyl-4'-cyanobiphenyl. This reference also discloses a method of preparing arylzinc halides from arylchlorides and arylbromides, including ones bearing various functional groups such as ester, nitrile, or ketone.

Carini et al., *J. Med. Chem.*, vol. 34 (1991), 2525–2547, cited above, discloses the preparation of 3-(4'-methylphenyl)benzonitrile by reacting 4-methylphenylzinc halide (prepared from 4-bromotoluene via 4-methylphenylmagnesium bromide, which is reacted with zinc chloride) and 3-bromobenzonitrile in the presence of bis(triphenylphosphine)nickel dichloride as precatalyst. U.S. Pat. No. 5,128,355 (to Carini et al.) similarly shows an equation (Scheme 14, Equation e) representing the nickel catalyzed cross coupling of a methylphenyizinc chloride (isomer unspecified) with a bromobenzonitrile (isomer unspecified) to give a methylphenylbenzonitrile (isomer unspecified). This method is exemplified only for the preparation of 2,6-dicyano-4'-methylbiphenyl from 2,6-dicyanophenylbromide (Example 343).

Mantlo et al., *J. Med. Chem.*, vol. 34 (1991), pp. 2919–2922 discloses the preparation of 2-(4'-methylphenyl) benzonitrile from 4-bromotoluene and 2-bromobenzonitrile according to the method (referenced) of Negishi et al.*J. Org. Chem.*, vol. 42 (1977), pp. 1821–1823. A zinc derivative was formed from the 4-bromotoluene and reacted with the 2-bromobenzonitrile in the presence of a catalytic amount of a dichlorobis(triphenylphosphine)nickel.

European Patent Application 470,794 discloses a process for preparing biphenylcarbonitriles in which a metal or organometallic 4-methylphenyl derivative is reacted with a bromo-, iodo-, or trifluoromethanesulphonyloxybenzonitrile in the presence of a palladium or nickel catalyst. The metal or organometallic 4-methylphenyl derivatives disclosed are of copper, lithium, tin, silicon, zirconium, aluminum, thallium, mercury, and magnesium. (Zinc is nowhere mentioned.) 4-methylphenyl derivatives of tributyltin are particularly preferred and are the only 4-methylphenyl derivatives shown by working example.

Only two of the working examples relate to the disclosed process for preparing biphenylcarbonitriles, Examples 1 and 2. Both involve reactions of the 4-methylphenyl tributyltin derivative with 2-bromobenzonitrile in the presence of tetrakis(triphenylphosphine)palladium. The 4-methylphenyl tributyltin derivatives are prepared by the reaction of the corresponding 4-methylphenyl magnesium bromide with tributyltin chloride, followed by separation and high vacuum distillation of the 4-methylphenyl tributyltin derivative. Example 2 shows the preparation of 4'-methylbiphenyl-2-carbonitrile (a.k.a. 2-(4'-methylphenyl)benzonitrile) by this method, involving a prolonged reaction time (36 hours) for the coupling reaction.

Percec et al. *J. Org. Chem.*, vol. 60 (1995), pp. 6895–6903 discloses reactions in which certain aryl mesylates are reacted with 1.8–2.0 equiv. of certain arylmagnesium halide or arylzinc halide reagents in the presence of 1.0 equiv. of zinc powder and a nickel phosphine complex as catalyst to form unsymmetrical biaryls in yields ranging from 31–60%.

Zembayashi et al., *Tetrahedon Letters,* vol 47 (1977), pp. 4089–4092 discloses reductive coupling of aryl bromides to the corresponding symmetrical biaryls by zinc powder in the presence of a nickel-phosphine complex as catalyst. The reference states, "Although the exact mechanism of the present coupling reaction has not yet been clarified, it seems likely that organozinc intermediates are not involved, but metallic zinc acts as a reducing agent for the Ni(II) species as mentioned above."

Colon et al.,*J. Org. Chem.*, vol. 51 (1986), pp. 2627–2637 and U.S. Pat. No. 4,263,466 (to Colon et al.) similarly discloses reductive coupling of aryl chlorides to the corresponding symmetrical biaryls by an excess of a reducing metal (Zn, Mg, or Mn) in the presence of a catalyst formed from an anhydrous nickel salt and triphenylphosphine. In an extensive exposition on the mechanism of the reaction, the authors conclude that the reducing metal serves to reduce the nickel salt and various arylnickel intermediates participating in the reaction. Nowhere do the authors make any mention of an arylzinc intermediate.

Kageyama et al., *Synlett,* 1994, pp. 371–2 discloses a procedure said to be advantageous "compared to the original Colon's method" (the reference discussed in the preceding paragraph herein) in which pyridine is used as solvent for the reductive coupling reaction affording symmetrical biaryls. This reference further discloses the extension of this procedure to reductive cross-coupling reactions of certain aryl halides (1 equiv.) in the presence of zinc powder (2 equiv.) and a nickel-phosphine catalyst in pyridine solvent to provide unsymmetrical biaryls. This reference is mainly concerned with the preparation of 4'-methylbiphenyl-2-carbonitrile-(also known as 2-(4'-methylphenyl) benzonitrile) by such reaction of 4-bromotoluene and 2-chlorobenzonitrile, which is reported to provide the desired unsymmetrical (cross-coupled) biaryl product in 69% yield. The two undesired symmetrical (homo-coupled) biaryl byproducts are formed in 11–12% yield each. Attempted reaction of 3-chlorotoluene with 2-chlorobenzonitrile did not afford the desired cross-coupled product, nor any homocoupled bitolyl. Only a 21% yield of the homocoupled bisbenzonitrile) is reported. There is no indication in the reference that the 4-chlorotoluene reacted at all.

A frequently used method of synthesizing biaryls containing electrophilic functional groups on a laboratory scale is the palladium catalyzed cross-coupling (Suzuki coupling), in which iodoaromatics, bromoaromatics, or aryl sulfonates are reacted with arylboronic acids or boronate esters in the presence of palladium catalysts and a base. An early report of this general reaction is Miyaura et al., *Synthetic Communications* vol. 11 (1981), 513. In this reference, chlorobenzene is reported to fail to react with phenylboronic acid using tetrakis(triphenylphosphine)palladium as catalyst in this system.

Ali et al., *Tetrahedron*, vol 48 (1992), pp. 8117–8126 discloses Suzuki-type cross-coupling reactions of arylboronic acids with pi-electron deficient heteroaryl chlorides (chloropyridines, chloropyrimidines, and chloropyrazines, chloroquinolines). These authors state, "It is widely accepted that palladium-catalyzed cross coupling reactions of arylboronic acids, and indeed of other organometallic species, proceed best with aryl or heteroaryl bromides or iodides, and either poorly, or more commonly, not at all with the corresponding chlorides." These investigators confirmed early literature reports that reaction of phenylboronic acid with either chlorobenzene or 3-chloropyridine in the presence of tetrakis(triphenylphosphine) palladium failed to produce any coupled product. Using Pd(bis-1,4-(diphenylphosphino)butane)Cl$_2$, however, they were able to get chlorobenzene to react to give 28% of biphenyl, and 3-chloropyridine was converted to 3-phenylpyridine in 71% yield. Among 2-chloropyridines, the reaction tolerated some (3-nitro, 5-chloro) but not other (3-OH, 3-CONH$_2$) substituents.

U.S. Pat. No. 5,130,439 discloses a process for preparing certain protected tetrazolyl biphenyls in which a protected tetrazolylphenylboronic acid or boronate derivative is reacted with a substituted phenyl bromide or iodide or a substituted sulfonyloxyphenyl derivative in the presence a base and a nickel, palladium or platinum catalyst, preferably palladium. Three of the working examples (Examples 4, 9, and 12) relate to the disclosed process for preparing the protected tetrazolyl biphenyls, and all involve reactions of triphenylmethyltetrazolylphenylboronic acid with a substituted (4-methyl, 4-hydroxymethyl, 4-formyl) bromobenzene in the presence of a tetrakis(triphenylphosphine)palladium catalyst and a carbonate base. This process has the disadvantage of requiring prior synthesis of the triphenylmethyltetrazolylphenylboronic acid This reference discloses a process for preparing the triphenylmethyltetrazolylphenylboronic acid from the corresponding bromobenzonitrile by reacting it with tributyltin chloride and sodium azide, then with triphenylmethyl chloride to form the triphenylmethyltetrazolylphenylbromide, which is reacted sequentially with n-butyllithium and triisopropylborate and the resulting boronate ester is finally hydrolyzed to the boronic acid. This reference illustrates that the nitrile group must be protected, in this case as the triphenylmethyltetrazolyl group, to be compatible with the use of an aryllithium intermediate in the overall process.

European Patent Application 470,795 discloses a process for preparing biphenylcarbonitriles in which a 4-methylphenyl boronic acid or boronate ester is reacted with a bromo-, iodo-, or trifluoromethanesulphonyloxy-benzonitrile in the presence of a palladium or nickel catalyst and a suitable base. Three of the working examples Examples 1, 2, and 6) relate to the disclosed process for preparing biphenylcarbonitriles, and all involve reactions of the 4-methylphenylboronic acid with 2-bromobenzonitrile in the presence of a palladium catalyst and sodium carbonate.

Saito et al., Tetrahedron Letters, vol 37 (1996), pp. 2993–2996 states, "The palladium-catalyzed cross-coupling reaction of arylboronic acids with aryl halides or triflates gives biaryls. High yields have been achieved with many substrates having various functional groups on either coupling partner, when using aryl bromides, iodides, or triflates as an electrophile. Chloroarenes are an economical and easily available, but they have been rarely used for the palladium catalyzed cross coupling reaction of arylboronic acids because of the oxidative addition of chloroarenes is too slow to develop the catalytic cycle. However, chloroarenes have been an efficient substrate for the nickel catalyzed cross coupling reaction with Grignard reagents . . . developed by Kumada and Tamao." This reference (Saito et al.) discloses syntheses of unsymmetrical biaryls by a nickel(0) catalyzed reaction of arylchlorides with arylboronic acids and tripotassium phosphate as the base at elevated temperatures.

U.S. Pat. No. 5,559,277 discloses a process for preparing biaryls by the Suzuki reaction of haloaromatics or arylsulfonates with arylboronates in the presence of a base and certain specific palladium compounds as catalysts. In addition to numerous bromoaromatics, reactions of chloroacetophenone and 2-chlorobenzonitrile are shown in working examples. All the working examples use at least 50% mole excess of the arylboronate relative to the haloaromatic and conduct the reaction for 16 hours at 130° C. The disclosed process also has the disadvantage of requiring the separate preparation of the arylboronate. Example 7 describes the preparation of 2-cyano-4-methylbiphenyl (a.k.a. 2-(4'-methylphenyl)benzonitrile) from 2-chlorobenzonitrile and 4-methylphenylboronic acid in 73% yield (49% yield on the 4-methylphenylboronic acid).

Kalinin, *Synthesis,* 1992, 413–432 reviews carbon-carbon bond formation to heteroaromatics using nickel and palladium catalyzed reactions. It shows numerous examples of the formation of unsymmetrical biaryls, wherein at least one of the aryl groups includes a heteroatom, including examples of palladium catalyzed reactions of arylbromides and aryliodides with arylzinc halides, palladium catalyzed reactions of chloropyridines with arylmagnesium halides, and nickel catalyzed reactions of arylchlorides and arylbromides with arylmagnesium halides. Nowhere does it show any example of a formation of an unsymmetrical biaryl by a reaction of an arylchloride with an arylzinc derivative.

U.S. Pat. No. 5,364,943 discloses the preparation of 3-amino-2-phenylpyridine and two 3-(substituted benzylamino)-2-phenylpyridine derivatives by the reaction of the corresponding 3-amino-2-chloropyridine or N-benzyl derivative with phenyl magnesium bromide in the presence of bis(phosphine)nickel dichloride complexes. For the parent compound (Example 7), a total of 4.4 eq. of phenylmagnesium bromide was reacted with 3-amino-2-chloropyridine and 0.5 eq. [bis(diphenylphosphino)ethane] nickel(II) chloride over the course of two days, to ultimately obtain a 48% of the isolated product.

OBJECTS OF THE INVENTION

The object of this invention is to provide an economically preferable, effective and efficient process for the preparation biaryl compounds. Further objects of this invention are to provide such a process having one or more of the following characteristics: 1) Capable of using inexpensive arylchlorides as reactants, rather than requiring arylbromides or aryliodides. 2) Capable of providing the biaryl compounds in high yield based on the arylchloride. 3) Capable of tolerating a variety of functional substituents on one or both of the aromatic reactants. 4) Minimizes the number of process reaction steps. 5) Minimizes the number of other process operations, including avoiding any need to isolate process intermediates, with attendant yield losses and other costs. 6) Readily scaleable for the production of commercial-scale quantities (10's to 10,000's of Kgs) of biaryl compounds. The present invention is directed towards one or more of the above objects. Other objects and advantages will become apparent to persons skilled in the art and familiar with the background references from a careful reading of this specification.

SUMMARY OF THE INVENTION

In its most basic terms, the present invention provide a process, having practical utility, for preparing biaryl compounds of the formula Ar-Ar', wherein Ar and Ar' are aryl groups and may be identical or different, comprising reacting an arylzinc reagent comprising the aryl group Ar bonded to zinc with an arylchloride of the formula Ar'Cl in the presence of a catalyst selected from the group consisting of nickel catalysts and palladium catalysts. The invention thereby provides a process that use an economically preferable arylchloride reactant to provide the Ar' group in the biaryl. The invention further provides a process compatible with a variety of functional substituents in the Ar' group, avoiding costs associated with protecting and deprotecting such substituents.

The present invention also provides a process capable of providing high yields of the desired biaryl compounds based on the arylchloride. Yields are typically above about 50% based on the arylchloride, preferably above about 60%, and most preferably above about 70%.

In certain embodiments of the present invention, the arylzinc reagent is prepared by reacting an a zinc salt with an arylmetal reagent capable of transferring the aryl group to the zinc salt. Suitable such arylmetal reagents include arylmagnesium reagents and aryllithium reagents. In certain such embodiments, an arylhalide comprising the Ar group is reacted with magnesium to form an arylmagnesium reagent, which is reacted with a zinc salt to produce the arylzinc reagent. Optionally, the arylmagnesium reagent and the arylzinc reagent may be prepared sequentially, without isolation, in a solution suitable for direct use in the biaryl preparation reaction. In certain of these embodiments, the arylhalide used to produce the arylzinc reagent is an arylchloride of the formula ArCl. The invention thereby provides a process for preparing biaryl compounds in which economically preferable arylchloride reactants provide both aryl groups in the biaryl compound.

In certain alternative embodiments of the present invention, the arylzinc reagent is produced by reacting an arylhalide with zinc. This method of preparing the arylzinc reagent is compatible with a variety of functional substituents in the Ar' group. The invention thereby provides a process for preparing biaryl compounds in which both aryl groups may comprise unprotected functional substituents.

In a specific preferred embodiment, the present invention provides a process for the preparation of 2-(4'-methylphenyl)benzonitrile comprising reacting a 4-methylphenylzinc reagent with 2-chlorobenzonitrile in the presence of a catalyst selected from the group consisting of nickel catalysts and palladium catalysts. The 4-methylphenylzinc reagent may be produced from 4-methylphenylchloride by its reaction with magnesium to form a 4-methylphenylmagnesium reagent, which is reacted with a zinc salt to produce the 4-methylphenylzinc reagent.

The invention thereby provides an efficient process for the preparation of 2-(4'-methylphenyl)benzonitrile from 4-methylphenylchloride and 2-chlorobenzonitrile.

DETAILED DESCRIPTION OF THE INVENTION

The present invention provides a process for the preparation of biaryl compounds of the formula Ar-Ar', wherein Ar and Ar' are aryl groups and may be identical or different. Suitable aryl groups Ar and Ar' include carbocyclic aryl groups, having only carbon atoms in the aromatic ring system and heterocyclic aryl groups, having one or more heteroatoms in the aromatic ring system. Typical carbocyclic aryl groups have 6–14 carbon atoms in the aromatic ring system. Preferred carbocyclic groups are phenyl and substituted phenyl groups. Typical heterocyclic aryl groups have 5–13 atoms in the aromatic ring system which comprises carbon atoms and one or more heteroatoms. Preferred heteroatoms are oxygen, sulfur, and nitrogen. Preferred heterocyclic aryl groups have 5 or 6 atoms in an aromatic ring comprising one or more heteroatoms selected from the group oxygen, sulfur, and nitrogen, benz-fused derivatives thereof, and substituted derivatives thereof. Examples of preferred heterocyclic aryl groups include pyridyl, furyl, thienyl, pyrrolyl, their benz-bused derivatives quinolinyl, isoquinolinyl, benzfuryl, benzyothienyl, indolyl, isoindolyl, and substituted derivatives thereof.

Suitable substituents in substituted aryl groups Ar and Ar' include alkyl (preferably $C_1$–$C_{12}$), alkenyl (preferably $C_1$–$C_{12}$), alkynyl (preferably $C_1$–$C_{12}$), alkoxy (preferably $C_1$–$C_{12}$), acyloxy (preferably $C_1$–$C_{12}$), aryloxy, aryl, heteroaryl, F, Cl, OH, $NO_2$, CN, COOH, CHO, $SO_3H$, $SO_2$, SOR, $NH_2$, NH-alkyl (preferably $C_1$–$C_{12}$ ), N-dialkyl (preferably $C_1$–$C_{12}$), trihalomethyl, NHCO-alkyl (preferably $C_1$–$C_8$), CONH-alkyl (preferably $C_1$–$C_4$), CON-dialkyl (preferably $C_1$–$C_4$), COO-alkyl (preferably $C_1$–$C_{12}$), $CONH_2$, CO-alkyl (preferably $C_1$–$C_{12}$), NHCOH, NHCOO-alkyl (preferably $C_1$–$C_8$), CO-aryl, COO-aryl, $CHCHCO_2$-alkyl (preferably $C_1$–$C_{12}$), $CHCHCO_2H$, PO-diaryl, and PO-dialkyl (preferably $C_1$–$C_8$).

In the process of the present invention, the biaryl compounds of the general formula Ar-Ar' are prepared by reacting an arylzinc reagent comprising the aryl group Ar bonded to zinc with an arylchloride of the formula Ar'Cl in the presence of a catalyst selected from the group consisting of nickel catalysts and palladium catalysts. Suitable arylzinc reagents are arylzinc species comprising the aryl group sigma bonded to zinc. Typical arylzinc reagents include those selected from the group consisting of arylzinc salts, arylzinc compounds, or mixtures thereof. Arylzinc salts are known in the art and have the general formula ArZnY, wherein Y is an inorganic or organic salt anion. The identity of the anion Y is not critical but it must not interfere with the reaction, which can be determined by routine experimentation. Preferred arylzinc salts are arylzinc halides of the general formula ArZnX, wherein X is a halide anion. Especially preferred are arylzinc chloride and arylzinc bromide reagents. Arylzinc compounds are known in the art and include monoarylzinc compounds and diarylzinc compounds. Examples of monoarylzinc compounds include compounds of the general formula ArZnR, wherein R is an organo group which does not interfere with the reaction. Preferred arylzinc compounds are diaryl zinc compounds having the general formula ArZn. Triarylzincate anions having the general formula $Ar_3Zn^-$ are also suitable arylzinc reagents.

The arylzinc reagents may be obtained by various methods known in the art. For examples, the corresponding arylhalide ArX, wherein X=Cl, Br, I, may be reacted with activated zinc to afford the corresponding arylzinc halide. A zinc salt may be reacted with a corresponding aryllithium reagent or arylmagnesium reagent to form the arylzinc reagent. Preferably, the zinc salt is reacted with one to two equivalents of aryllithium or arylmagnesium reagent to form the arylzinc salt, the diarylzinc compound, or mixtures thereof. (An aryllithium reagent or an arylmagnesium salt comprises one aryl equivalent; a zinc salt is reacted with one of them in a mole ratio of 1:1 to 1:2. A diarylmagnesium reagent comprises two aryl equivalents; a zinc salt is reacted with it in a mole ratio of 0.5:1 to 1:1.) Suitable zinc salts for these preparations include salts having the general formula $ZnY_2$, wherein Y is defined as above. Preferred zinc salts are the zinc halides $ZnX_2$, wherein X is a halide ion. Especially preferred are zinc chloride and zinc bromide.

Suitable arylmagnesium reagents for the preparation of arylzinc reagents are selected from the group consisting of arylmagnesium salts, diarylmagnesium compounds, or mixtures thereof. Arylmagnesium salts have the general formula ArMgY, wherein Y is defined as above. Preferred arylmagnesium salts are arylmagnesium halides, also known as aryl Grignard reagents, of the general formula ArMgX, wherein X is a halide anion. Especially preferred are La arylmagnesium chloride and arylmagnesium bromide reagents. Diaryl magnesium compounds have the general formula $Ar_2Mg$. Arylmagnesium halides and diarylmagnesium compounds can be prepared from arylhalides and magnesium by methods known in the art.

Suitable nickel and palladium catalysts for the process of the invention include those provided by nickel and palladium compounds and salts, in particular nickel(0) and palladium(0) compounds and nickel(II) and palladium(II) compounds and salts. Preferably, the catalyst also comprises a ligand. Suitable ligands include monodentate, bidentate, and tridentate ligands comprising nitrogen or phosphorus as ligating atom. Preferred ligands are triorganophosphine, triorganophosphite, and aromatic nitrogen heterocycle ligands. Examples of preferred ligands include triarylphosphines (e.g. triphenylphosphine), bidentate bis(diarylphosphino) compounds (e.g. 1,1'-bis(diphenylphosphino)ferrocene), trialkylphosphites (e.g. triisopropylphosphite), and pyridine-type ligands (e.g. pyridine, bipyridine). Particular ligands include those illustrated in the working Examples herein.

Suitable and optimal ratios of the ligand to catalyst metal depend on a number of other parameters, including the catalyst metal, whether nickel or palladium, the identity of the ligand, the concentration of the catalyst, the reaction temperature, the reactivity of the reactants, the solvent, and the like, and can be readily determined by routine experimentation. Typically the ratio of the ligand to the catalyst metal is in the range of 1:1 to 4:1. However, the amount of ligand in the reaction mixture may be in excess of the maximum ratio that could be bound to the catalyst metal.

The active catalyst may be prepared in advance of its introduction to the reaction mixture, or may be generated in the reaction mixture. It is believed that the active catalyst in the reaction is a nickel(0) or palladium(0) compound. The active catalyst may be provided by a preformed ligated nickel(0) or palladium(0) compound (e.g. tetrakis(triphenylphosphine)palladium(0), bis(triphenylphosphine)nickel(0) dicarbonyl) or may be provided by combining in solution, either ex situ or in situ to the reaction mixture, a suitable ligand with a suitable nickel(0) or palladium(0) source (e.g. bis(1,5-cyclooctadiene)nickel(0), tris(dibenzylideneacetone)palladium(0)). When the catalyst is provided by a nickel(II) or palladium(II) compound or salt, the active catalyst is provided by its reduction either ex situ or in situ to the reaction mixture. Generally, the arylzinc reagent in the reaction mixture is capable of reducing the nickel(II) or palladium(II) to generate the active catalyst in situ, with concomitant generation of the symmetrical biaryl Ar—Ar. This can be determined by routine experimentation. Suitable reductants for ex situ generation of the active catalyst from nickel(II) and palladium(II) sources are known in the art and include organomagnesium halide reagents (e.g. methylmagnesium halide) and various hydride reagents (e.g. sodium bis(2-methoxyethoxy)aluminum dihydride). Preferably the nickel(II) or palladium(II) is combined with ligand prior to its reduction. The nickel(II) or palladium(II) may be provided as a preformed ligated nickel(II) or palladium(II) compound (e.g. dichlorobis(triphenylphosphine)nickel(II), dichloro[1.1'-bis(triphenylphosphino)ferrocene]palladium (II) or may be provided by combining in solution a suitable ligand with a suitable nickel(II) or palladium(II) compound (e.g. dichlorobis(acetonitrile)palladium(II) or salt. Suitable nickel(II) and palladium(II) salts include the salts having the general formula $NiY_2$ and $PdY_2$, wherein Y is defined as above. Preferred nickel(II) or palladium(II) salts include the chlorides, bromides, carboxylates (e.g. formate, acetate, stearate) and acetylacetonates. Generally, anhydrous nickel and palladium salts are preferred. In certain embodiments, however, it has been surprisingly found that a small amount of water in the salt can be beneficial to the catalyst activity. Whether an amount of water is beneficial or detrimental in a specific embodiment can be determined by routine experimentation.

The reaction of the arylzinc reagent with the arylchloride may be conducted without solvent or with an additional solvent that is reaction-inert. By reaction-inert solvent is meant a solvent system which does not react with the reactants or products of the reaction, or react unfavorably with the catalyst. The term solvent system is used to indicate that a single solvent or a mixture of two or more solvents can be used. Representative solvents are aromatic hydrocarbons such as benzene, toluene, xylene; aliphatic hydrocarbons such as pentane, hexane, heptane; acetonitrile; dialkyl ethers; and cyclic ethers, and mixtures thereof. The solvent system used need not bring about complete solution of the reactants.

Preferred solvents in the solvent system are ether solvents, including diethyl ether, diisopropyl ether, dibutylether, methyl-t-butylether, dimethoxyethane, diglyme, dibutyldiglyme, tetrahydrofuran, dioxane, and the like. It is generally preferred that the solvent system is anhydrous. In certain embodiments, however, it has been surprisingly found that a small amount of water can be beneficial to the catalyst activity. Whether small amounts of water are advantageous or detrimental in a specific embodiment can be determined by routine experimentation.

The ratio of the arylzinc reagent to the arylchloride is not critical. Either reactant may be the limiting reactant and this choice can respond to other considerations, such as which is the more costly reactant to provide and which homocoupled by-product is more readily separated or removed to an acceptable level from the desired cross-coupled product. Generally the ratio of equivalents of arylzinc reagent to mole of arylchloride ranges from 0.5:1 to 2:1. One mole of diarylzinc reagent is counted as two equivalents of arylzinc reagent. In typical embodiments, this ratio is in the range 1:1 to 1.5:1.

The mole ratio of the catalyst to the arylchloride to be reacted is not critical, but should be a catalytic ratio less than about 1:10. The minimum amount of catalyst relative to the arylchloride depends on the activity of the specific catalyst composition, the specific arylchloride and arylzinc reagent to be reacted, the reaction temperature, the concentration of the reactants and catalyst in the solution, and the maximum time allowed for completion of the reaction, and can be readily determined by routine experimentation. In typical embodiments, a suitable mole ratio of the catalyst metal, nickel or palladium, to arylchloride is in the range of 1:1000 to 1:10.

In typical embodiments, the reaction is suitably conducted at a temperature of from about 20° C. to 100° C., although higher temperature may be used in some embodiments.

The order of addition of the reaction components is not critical. All the reaction components can be added prior to any heating to the reaction temperature, or one or more components may be added when the other components have be brought to the desired reaction temperature. The preferred order of addition for any specific embodiment can be determined by routine experimentation with a view towards both reaction performance and chemical engineering considerations.

The desired biaryl compound is recovered by known methods.

The present invention specifically provides a process for the preparation of 2-(4'-methylphenyl)benzonitrile comprising reacting a 4-methylphenylzinc reagent with 2-chlorobenzonitrile in the presence of a catalyst selected from the group consisting of nickel catalysts and palladium catalysts. The preferred 4-methylphenylzinc reagent is 4-methylphenyizinc chloride, di(4-methylphenyl)zinc or mixtures thereof. This preferred 4-methylphenylzinc reagent may be suitably prepared from 4-methylphenylchloride by its reaction with magnesium to form a 4-methylphenylmagnesium reagent, which is reacted with zinc chloride to produce the 4-methylphenylzinc reagent.

The preferred catalyst for this application is provided by a nickel salt, preferably nickel bis(acetylacetonate), and a triorganophosphine or triorganophosphite ligand, preferably a trialkylphosphite, and preferably in a mole ratio of 1:1 to 4:1 phosphorus to nickel. The reaction of the 4-methylphenylzinc chloride with the 2-chlorobenzonitrile in the presence of the catalyst is preferably conducted in tetrahydrofuran at a temperature of about 40 to 70° C.

In one practical embodiment, 4-methylphenylchloride in tetrahydrofuran solvent is reacted with magnesium to form 4-methylphenylmagnesium chloride. An equivalent of zinc chloride is added to this mixture to form 4-methylphenylzinc chloride. This mixture is then combined with the 2-chlorobenzonitrile and the nickel catalyst components and reacted to form the 2-(4'-methylphenyl)benzonitrile.

EXAMPLES OF THE INVENTION

Without further elaboration, it is believed that one skilled in the art can, using the preceding description, utilize the present invention to its fullest extent. The following specific examples are intended merely to illustrate the invention and not to limit the scope of the disclosure or the scope of the claims in any way whatsoever.

Example 1

Preparation of 4-phenylbenzonitrile by nickel catalyzed reaction of phenylzinc chloride with 4-chlorobenzonitrile: A solution of 1.77 g (13.0 mmol) zinc chloride in 25 mL of tetrahydrofuran (THF) was treated at 0° C. with 6.94 mL (12.5 mmol) of 1.80 M phenyllithium in cyclohexane-diethylether. The resulting mixture was warmed to room temperature and stirred for 15 minutes to complete the preparation of the phenylzinc chloride reagent mixture.

The nickel catalyst was prepared separately as follows: 0.128 g (0.50 mmol) nickel bis(acetylacetonate) (containing <1 wt % water) and 0.523 g (2.00 mmol) triphenylphosphine were dissolved in 5 mL THF. The resulting dear solution was treated with 18 µL (1.0 mmol) water, cooled to 0° C., and further treated with 0.28 mL (0.50 mmol) of 35% (ca. 1.8 M) sodium bis(2-methoxyethoxy)aluminum dihydride in THF. The dark reddish brown solution was warmed to room temperature to complete the preparation of the nickel catalyst solution.

The nickel catalyst solution was added at room temperature to the phenylzinc chloride reagent mixture. 1.38 g (10.0 mmol) of 4-chlorobenzonitrile and 0.73 mL (3.0 mmol) of tridecane (internal GC standard) were added sequentially to the resulting mixture, which was then stirred for 1 h at 25° C. A sample was withdrawn from the reaction mixture and quenched in a mixture of ether and 1 N HCl. GC analysis of the organic phase of the hydrolyzed reaction sample showed the presence of 8.1 mmol of 4-phenylbenzonitrile (81% chemical yield on 4-chlorobenzonitrile; identity confirmed by GC-MS) and no remaining 4-chlorobenzonitrile in the reaction mixture.

This Example illustrates the process of the instant invention wherein an unsymmetrical biaryl is prepared in high yield by reacting an arylzinc reagent with an arylchloride in the presence of a nickel catalyst. This Example also illustrates preparation of an arylzinc halide reagent from the corresponding aryllithium reagent and a zinc salt and illustrates a nickel catalyst provided by combining ex situ a nickel salt, a ligand, and a reducing agent.

Comparative Example 1

Attempted preparation of 4-phenylbenzonitrile by nickel catalyzed reaction of phenyllithium with 4-chlorobenzonitrile: The procedure was identical to Example 1, with the exception that no zinc chloride was provided to the solution prepared from phenyllithium in cyclohexane-diethylether and THF and the resulting phenyllithium solution was used in place of the phenylzinc chloride reagent mixture. GC analysis of the organic phase of a hydrolyzed reaction sample taken after 4 h of reaction time at room temperature showed the presence of 0.11 mmol of 4-phenylbenzonitrile (1% chemical yield on 4-chlorobenzonitrile) and 0.85 mmol (8.5%) remaining 4-chlorobenzonitrile in the reaction mixture. No other significant products were observed by the GC method.

This Example illustrates that the reaction of the aryllithium reagent with the chlorobenzonitrile in the presence of the nickel catalyst did not produce any useful amount of the desired biarylnitrile. Presumably, the preponderance of the chlorobenzonitrile reacted with the aryllithium reagent at the nitrile group to give products that either did not partition into the organic layer of the hydrolyzed reaction sample or were too nonvolatile for detection by the GC method. By comparison, Example 1 shows the more rapid conversion of the chlorobenzonitrile and the practical high yield of the desired biarylnitrile provided by the present invention wherein the arylzinc reagent is first made from, and then used in place of, the aryllithium reagent.

Example 2

Preparation of 4-(4'-methylphenyl)propiophenone by nickel catalyzed reaction of 4-methylphenylzinc chloride with 4-chloropropiophenone: The procedure was identical to Example 1, with the exceptions that 1.68 g (10.0 mmol) 4-dichloropropiophenone was reacted instead of 4-chlorobenzonitrile and the arylzinc chloride reagent mixture was prepared as follows: 7.8 mL (12.5 mmol) of 1.60 M 4-methylphenylmagnesium chloride in THF was treated with 1.77 g (13.0 mmol) of zinc chloride. The reaction was conducted at room temperature in the presence of the nickel catalyst provided as in Example 1. GC analysis of a hydrolyzed reaction sample taken after 1 h of reaction time showed the presence of 8.5 mmol of 4-(4'-methylphenyl) propiophenone (85% chemical yield on 4-chloropropiophenone; identity confirmed by GC-MS) and no remaining 4-chloropropiophenone in the reaction mixture.

This Example illustrates preparation of an arylzinc halide reagent from the corresponding arylmagnesium halide reagent and a zinc salt for use in the process of the present invention.

Comparative Example 2

Attempted preparation of 4-(4-methylphenyl) propiophenone by nickel catalyzed reaction of 4-methylphenylmagnesium chloride with 4-chloropropiophenone: The procedure was identical to Example 2, with the exception that no zinc chloride was added to the solution of 4-methylphenylmagnesium chloride in THF, which was used directly in the reaction. GC analysis of the hydrolyzed reaction sample taken after 1 h of reaction time at room temperature showed the presence of 0.69 mmol of 4-(4'-methylphenyl)propiophenone (6.9% chemical yield on 4-chloropropiophenone), 0.47 mmol (4.7%) remaining 4-chloropropiophenone, and 6.5 mmol of 1-(4-methylphenyl)-1(4-chlorophenyl)propanol (65% chemical yield on 4-chloropropiophenone; identity confirmed by GC-MS) in the reaction mixture.

This Example illustrates that the reaction of the arylmagnesium halide reagent with the chlorophenyl alkyl ketone in the presence of the nickel catalyst did not produce any useful amount of the desired biaryl alkyl ketone. Instead, the reaction produced predominantly the product of the direct addition of the arylmagnesium halide reagent with the keto group. By comparison, Example 2 illustrates the practical high yield of the desired biaryl alkyl ketone provided by the present invention wherein the arylzinc halide reagent is first made from, and then used in place of, the arylmagnesium halide reagent. This comparison illustrates the compatibility of the process of the instant invention with functional groups that are reactive to arylmagnesium halide reagents.

Example 3

Preparation of methyl 4-(4'-methylphenyl)benzoate by nickel catalyzed reaction of 4-methylphenylzinc chloride with methyl 4-chlorobenzoate: The procedure was identical to Example 2, with the exception that 1.71 g (10.0 mmol) of methyl 4-chlorobenzoate was reacted instead of 4-chloropropiophenone and the reaction temperature was 50° C. GC analysis of a hydrolyzed reaction sample taken after 1.5 h reaction time showed the presence of 8.1 mmol of methyl 4-(4-methylphenyl)benzoate (81% chemical yield on methyl 4-chlorobenzoate; identity confirmed by GC-MS) and 0.18 mmol (1.8%) remaining methyl 4-chlorobenzoate.

This Example illustrates the process of the present invention for reaction of an arylzinc halide reagent, derived from an arylmagnesium halide reagent, with another arylchloride bearing a functional group (ester) that can react directly with the arylmagnesium halide reagents.

Comparative Example 3

Attempted preparation of methyl 4-(4'-methylphenyl) benzoate by nickel catalyzed reaction of 4-methylphenylmagnesium chloride with methyl 4-chlorobenzoate: The procedure was identical to Example 3, with the exception that no zinc chloride was added to the solution of 4-methylphenylmagnesium chloride in THF, which was used directly in the reaction. GC analysis of the hydrolyzed reaction sample taken after 3 h of reaction time at 50° C. showed the presence of 0.57 mmol methyl 4-(4'-methylphenyl)benzoate (5.7% chemical yield on methyl 4-chlorobenzoate) and 3.2 mmol (32%) remaining methyl 4-chlorobenzoate. No other significant reaction products were observed by the GC method.

This Example illustrates that the reaction of the arylmagnesium halide reagent with the chlorobenzoate ester in the presence of the nickel catalyst did not produce any useful amount of the desired biarylcarboxylate ester. Presumably, the consumed benzoate ester that is not accounted for by the GC observable products was consumed by the typical reaction of two moles of arylmagnesium halide reagent with 1 mole of benzoate ester group to produce, after hydrolysis, a 1,1',1,"triarylcarbinol, which is too nonvolatile for observation by the GC method. By comparison, Example 3 shows the practical high yield of the desired biarylcarboxylate ester provided by the present invention wherein the arylzinc halide reagent is first made from, and then used in place of, the arylmagnesium halide reagent. This comparison further illustrates the compatibility of the process of the instant invention with functional groups that are reactive to arylmagnesium halide reagents.

Example 4

Preparation of 2-(4'-methylphenyl)benzonitrile by nickel catalyzed reaction of 4-methylphenylzinc chloride with 2-chlorobenzonitrile: 3.95 mL (7.50 mmol) of 1.90 M 4-methylphenylmagnesium chloride in THF was treated with of 1.09 g (8.00 mmol) of zinc chloride. The resulting 4-methylphenylzinc chloride reagent mixture was treated with a solution of 0.688 g (5.00 mmol) 2-chlorobenzonitrile, 0.0964 g (0.375 mmol) nickel acetylacetonate (containing 5 wt % water) and 0.19 mL (0.75 mmol) triisopropyl phosphite. The mixture was heated to 40° C. for reaction. GC analysis of a hydrolyzed reaction sample taken after 6 h reaction showed the presence of 4.44 mmol of 2-(4'-methylphenyl)benzonitrile (89% chemical yield on 2-chlorobenzonitrile) and 0.04 mmol (0.7%) remaining 2-chlorobenzonitrile in the reaction mixture.

This Example illustrates the process of the present in invention for the preparation of 2-(4'-methylphenyl) benzonitrile from 2-chlorobenzonitrile. It further illustrates a nickel catalyst provided in situ by a nickel(II) salt and a suitable ligand.

Comparative Example 4

Attempted preparation of 2-(4'-methylphenyl)benzonitrile by nickel catalyzed reaction of 4-methylphenylmagnesium chloride with 2-chlorobenzonitrile: The procedure was identical to Example 4, with the exception that no zinc chloride was added to the solution of 4-methylphenylmagnesium chloride in THF, which was used directly in the reaction. GC analysis of a hydrolyzed reaction sample taken after 6 h reaction time at 40° C. showed the presence of 0.80 mmol of 2-(4-methylphenyl)benzonitrile (16% chemical yield on 2-chlorobenzonitrile) and 0.52 mmol (10%) remaining 2-chlorobenzonitrile. No other significant reaction products were observed by the GC method.

This Example illustrates that the reaction of 4-methylphenylmagnesium chloride with 2-chlorobenzonitrile in the presence of a nickel catalyst is not useful for the preparation of 2-(4-methylphenyl) benzonitrile. Presumably, the preponderance of the 2-chlorobenzonitrile reacted with the 4-methylphenylmagnesium chloride at the nitrile group to give products that either did not partition into the organic layer of the hydrolyzed reaction sample or were too non-volatile for detection by the GC method By comparison, Example 4 shows the practical high yield of 2-(4'-methylphenyl)benzonitrile provided by the present invention wherein the 4-methylphenylzinc chloride is first made from, and then used in place of, the 4-methylphenylmagnesium chloride.

Example 5

Preparation of 4-phenylbenzonitrile by nickel catalyzed reaction of diphenylzinc with 4-chlorobenzonitrile (1.1:1.0 mole ratio): To a nickel catalyst solution prepared as described in Example 1 (scaled to 0.10 mmol nickel) was added 12.0 mL (2.20 mmol) of 0.183 M diphenylzinc in THF. 0.275 g (2.00 mmol) of 4-chlorobenzonitrile and 0.15 mL (0.60 mmol) of tridecane (internal standard for GC analysis) were sequentially added at room temperature, which was then stirred for 1 h at 25° C. GC analysis of a hydrolyzed reaction sample showed the presence of 1.60 mmol of 4-phenylbenzonitrile (80% chemical yield on 4-chlorobenzonitrile; identity confirmed by GC-MS) and no remaining 4-chlorobenzonitrile.

This Example illustrates the use of a diarylzinc reagent in the process of the present invention.

Example 6

Preparation of 4-phenylbenzonitrile by nickel catalyzed reaction of diphenylzinc with 4-chlorobenzonitrile (0.6:1.0 mole ratio): The procedure was identical to Example 5, with the exception that only 6.83 mL (1.25 mmol) of the 0.183 M solution of diphenylzinc in THF was used. GC analysis of a hydrolyzed reaction sample taken after 2 h at room temperature showed the presence of 1.67 mmol (84%) of 4-phenylbenzonitrile (84% chemical yield on 4-chlorobenzonitrile) and no remaining 4-chlorobenzonitrile.

This Example illustrates that both aryl groups in diarylzinc reagents can react with the arylchloride to make biaryl compounds in the process of the present invention.

Example 7

Preparation of 2-(4'-methylphenyl)benzonitrile by nickel catalyzed reaction of 4-methylphenylzinc chloride with 2-chlorobenzonitrile: To a solution of 17.3 g (127 mmol) zinc chloride in 135 mL of THF at 0° C. was added 88.2 mL (127 mmol) 1.44 M 4-methylphenylmagnesium chloride in THF. The resulting white slurry was warmed to room temperature and stirred for 15 minutes to complete the preparation of 4-methylphenylzinc chloride.

Separately, 5.66 g (7.5 mmol) nickel stearate (contained ca. 17% stearic acid) was dissolved in 30 mL of THF and the solution treated with 3.70 mL (15.0 mmol) of triisopropyl phosphite. The resultant clear solution was treated sequentially at room temperature with 15.0 mL of the 4-methylphenylzinc chloride mixture and then 13.8 g (100 mmol) of 2-chlorobenzonitrile. The reaction mixture was heated to 50° C., and the remaining 4-methylphenylzinc chloride slurry was added to it over the course of 75 minutes. Upon completion of the addition, the mixture was stirred at 50° C. for an additional 1.5 h. GC analysis of a hydrolyzed reaction sample (with dodecane was added as a GC reference standard) showed the presence of 80.5 mmol (80.5%) of 2-(4-methylphenyl)benzonitrile (80.5% chemical yield on 2-chlorobenzonitrile) and 1.97 mmol (1.97%) remaining 2-chlorobenzonitrile.

This Example illustrates the use of another nickel salt for the in situ generation of the active nickel. It also illustrates the use of the arylzinc reagent to reduce the nickel(II) catalyst precursor. It further illustrates the reverse order of addition of the arylzinc reagent to the solution of the arylchloride and the nickel catalyst.

Example 8

Preparation of 2-(4'-methylphenyl)thiophene by nickel catalyzed reaction of 4-methylphenylzinc chloride with 2-chlorothiophene: The procedure was identical to Example 2 with the exception that 0.92 mL (10 mmol) 2-chlorothiophene was reacted instead of 4-chloropropiophenone with the 4-methylphenylzinc chloride reagent (derived from 1.77 g (13.0 mmol) of zinc chloride and 7.8 mL (12.5 mmol) of 1.60 M p-tolylmagnesium chloride in THF) in the presence of the nickel catalyst prepared in Example 1. GC analysis of a hydrolyzed reaction sample taken after 1 h at room temperature showed the presence of 6.3 mmol of 2-(4'-methylphenyl)thiophene (63% chemical yield based on 2-chlorothiophene; identity confirmed by GC-MS) and no remaining 2-chlorothiophene.

This Example illustrates the preparation of a biaryl compound comprising a heterocyclic aryl group (thienyl) by the process of the present invention.

Example 9

Preparation of 3-amino-2-phenylpyridine by nickel catalyzed reaction of phenylzinc halide with 3-amino-2-chloropyridine: To a solution of 24.5 g (180 mmol) zinc chloride in 120 mL of THF was added 170 mL (170 mmol; 2.1 equivalents) 1.0 M phenylmagnesium bromide in THF, and the resulting mixture stirred at room temperature for 30 minutes. This phenylzinc halide mixture was then treated sequentially with a mixture of 3.14 g (4.8 mmol; 0.06 equivalents) dichlorobis(triphenylphosphine)nickel suspended in 60 mL of THF and 10.3 g (80.0 mmol; 1.0 equivalents) 3-amino-2-chloropyridine dissolved in 20 mL of THF. The reaction mixture was stirred at room temperature for 3 h and then it was poured into a stirred mixture of 300 mL 1 N HCl and 150 mL of ethyl acetate. After stirring 15 minutes, the phases were separated and the organic phase was extracted with 5×150 mL of 1 N HCl. The combined acidic aqueous solution was back-extracted with 2×100 mL of ethyl acetate. The aqueous solution was then made basic by the addition of 600 mL of 50% NaOH and extracted with 5×200 mL of ethyl acetate. The combined ethyl acetate extract was washed with saturated aqueous NaCl. After drying over anhydrous $MgSO_4$, evaporation of the ethyl acetate solution gave 12.7 g of crude product as a viscous golden-yellow oil. HPLC analysis showed the oil comprised a 95:4:1 molar ratio of 3-amino-2-phenylpyridine, 3-aminopyridine, and 3-amino-2-chloropyridine, respectively. The crude product was dissolved with heating in 2:1 pentane:toluene. This solution was treated with ca. 2 g of activated carbon, filtered, and then let cool to room temperature. Upon reaching room temperature, the solution was seeded with a few crystals of 3-amino-2-phenylpyridine. After 3 h at room temperature, the off-white crystalline product was collected by filtration. Two additional crops of product were collected from concentration of the mother liquor to afford a total of 9.78 g of 3-amino-2-phenylpyridine, m.p. 65–67° C. (72% recovered yield on 3-amino-2-chloropyridine).

This Example again illustrates the preparation of a biaryl compound comprising a heterocyclic aryl group (pyridyl) by the process of the present invention. It also illustrates the in situ provision of an active nickel catalyst by a ligated nickel(II) compound. Comparison with Example 7 of U.S. Pat. No. 5,364,943, which used 4.4 eq. equivalents of phenylmagnesium bromide and 0.5 eq. of nickel catalyst to react 3-amino-2-chloropyridine over the course of two days to ultimately obtain a 48% of the isolated product, shows the very substantially increased reaction efficiency, catalytic activity, and yield that are provided by the present invention wherein the arylzinc halide reagent is first made from, and then used in place of, the arylmagnesium halide reagent.

Example 10

Preparation of 3-amino-2-phenylpyridine by nickel catalyzed reaction of phenylzinc chloride with 3-amino-2-chloropyridine: To a solution of 1.64 g (12.0 mmol) zinc chloride in 10 mL of pyridine was added 5.8 mL (11 mmol) 1.88 M phenylmagnesium chloride in THF, and the mixture was stirred at room temperature for 30 minutes. This phenylzinc chloride mixture was then treated sequentially with 0.128 g (0.500 mmol) nickel bis(acetylacetonate) and 0.64 g (5.0 mmol) 3-amino-2-chloropyridine and heated to 50° C. HPLC analysis of a hydrolyzed reaction sample taken after 3 h at 50° C. showed the molar ratio of 3-amino-2-phenylpyridine to 3-amino-2-chloropyridine to be 97:3.

This Example illustrates the in situ generation of the active nickel catalyst from a nickel(II) salt and an aromatic nitrogen heterocycle ligand, pyridine. Comparison with Example 7 of U.S. Pat. No. 5,364,943 again illustrates the very substantially increased reaction efficiency, catalytic activity, and yield that are provided by the present invention wherein the arylzinc halide reagent is first made from, and then used in place of, the arylmagnesium halide reagent.

Example 11

Preparation of 4-phenyltoluene by nickel catalyzed reaction of phenylzinc chloride with 4-chlorotoluene: Phenylzinc chloride (6.25 mmol) was prepared in THF by the addition of 3.32 mL (6.25 mmol) 1.88 M phenylmagnesium chloride to a solution of 1.02 g (7.5 mmol) zinc chloride in 12 mL THF at 0° C., followed by warming to room temperature for one-half hour. 0.59 mL (5.0 mmol) 4-chlorotoluene and a solution of 0.065 g (0.10 mmol) dichlorobis(triphenylphosphine)nickel and 0.052 g (0.20 mmol) triphenylphosphine in 5 mL of THF were sequentially added to the phenylzinc chloride mixture. The reaction mixture was heated to 50° C. and held at that temperature for 24 h. GC analysis (using dodecane as an internal reference standard) of a hydrolyzed reaction sample showed the presence of 3.68 mmol of 4-phenyl-toluene (74% chemical yield on 4-chlorotoluene) and 0.25 mmol (5%) remaining 4-chlorotoluene in the reaction mixture.

This Example illustrates the preparation of a biaryl compound using an carbocyclic arylchloride that does not contain any activating functional group. It also illustrates the in situ generation of the active nickel catalyst from a nickel compound and additional ligand.

Example 12

Preparation of 4-diphenyltoluene by nickel catalyzed reaction of phenylzinc chloride with 4-chlorotoluene: The procedure was identical to Example 11, with the exceptions that the nickel was provided by 0.026 g (0.310 mmol) nickel bis(acetylacetonate) and the ligand was provided by 0.062 g (0.10 mmol) 1,1,1-tris(diphenylphosphinomethyl)ethane. After heating the reaction mixture for 18 h at 50° C., GC analysis (using dodecane as an internal reference standard) of a hydrolyzed reaction sample showed the presence of 4.58 mmol of 4-phenyltoluene (92% yield on 4-chlorotoluene) and 0.15 mmol (3%) remaining 4-chlorotoluene in the reaction mixture.

This Example further illustrates the high yield preparation of a biaryl compound using an carbocyclic arylchloride that does not contain any activating functional group. This Example also illustrates the in situ generation of the active nickel catalyst from a nickel salt and added ligand and a catalyst comprising a tridentate chelating ligand.

Example 13

Preparation of 2,2'-dicyanobiphenyl by nickel catalyzed reaction of 2-cyanophenylzinc bromide with 2-chlorobenzonitrile: Activated zinc was prepared and reacted with 2-bromobenzonitrile to provide 2-cyanophenylzinc bromide, as follows: A mixture of 0.208 g (30.0 mmol) lithium wire and 3.91 g (30.5 mmol) naphthalene in 15 mL of THF was stirred at room temperature for 4 h. To the resultant dark green solution was then added a solution of 2.04 g (15.0 mmol) zinc chloride in 15 mL of THF. After stirring the mixture for 10 minutes, 0.91 g (5.0 mmol) 2-bromobenzonitrile was added and the reaction mixture refluxed for 8 h. The resultant mixture was then filtered through a small pad of celite under nitrogen to provide a clear, dark solution of 2-cyanophenylzinc bromide.

The 2-cyanophenylzinc bromide solution was treated with 0.55 g (4.0 mmol) 2-chlorobenzonitrile followed by a solution containing 0.077 g (0.3 mmol) nickel acetylacetonate (containing <1% water), 0.15 mL (0.6 mmol) triisopropyl phosphite, and 5.4 µL (0.30 mmol) water in 3 mL THF. After heating the mixture for 24 h at 55° C., GC analysis of a hydrolyzed sample (after adding dodecane as an internal GC reference standard) showed the presence of 2.03 mmol of 2,2'-dicyanobiphenyl (51% chemical yield on 2-chlorobenzonitrile), 1.85 mmol (46%) remaining 2-chlorobenzonitrile, and 1.56 mmol (31%) of benzonitrile in the reaction mixture.

This Example illustrates generation of an arylzinc reagent by reaction of activated zinc with an arylhalide. It also illustrates the preparation of a biaryl compound with a reactive functional group on each of the aryl groups. It further illustrates the preparation of a symmetrical biaryl compound.

Example 14

Preparation of 2-(4'-methylphenyl)benzonitrile by nickel catalyzed reaction of 2-cyanophenylzinc bromide with 4-chlorotoluene: A clear THF solution of 2-cyanophenylzinc bromide was prepared from 5.0 mmol of 2-bromobenzonitrile by the procedure described in Example 13. To this solution was sequentially added 0.47 mL (4.0 mmol) 4-chlorotoluene and a solution containing 0.20 g (0.30 mmol) dichlorobis(triphenylphosphine)nickel and 0.16 g (0.60 mmol) of triphenylphosphine in 2.5 mL of THF. After heating the reaction mixture for 5 h at 55° C., GC analysis of a hydrolyzed reaction sample (after adding dodecane as an internal GC reference standard) showed the presence of 2.94 mmol 2-(4-methylphenyl)benzonitrile (75% chemical yield on 4-chlorotoluene) in the reaction mixture.

This Example illustrates the preparation of 2-(4-methylphenyl)benzonitrile wherein the arylzinc reagent delivers the cyanophenyl group and the arylchloride delivers the 4-methylphenyl group, which is opposite the approach illustrated in the other Examples herein for the preparation of 2-(4'-methylphenyl)benzonitrile. It further illustrates the use of an arylzinc reagent comprising a reactive functional group (cyano) incompatible with arylmagnesium reagents and the use of a carbocyclic arylchloride that does not contain any activating functional group (like cyano).

Example 15

Preparation of 4-(4'-methylphenyl)benzonitrile by palladium catalyzed reaction of 4-methylphenylzinc chloride with 4-chlorobenzonitrile: A solution of 1.77 g (13.0 mmol) zinc chloride in 25 mL of THF was treated at 0° C. with 7.80 mL (12.5 mmol) 1.60 M 4-methylphenylmagnesium chloride in THF, and the resulting mixture was warmed to room temperature and stirred for 30 minutes to complete the preparation of the 4-methylphenylzinc chloride reagent. This mixture was then treated sequentially with 1.38 g (10.0 mmol) 4-chlorobenzonitrile, 0.408 g (0.500 mmol) [1,1'-bis(diphenylphosphino)ferrocene]dichloropalladium-dichloromethane complex, and 0.73 mL (3.0 mmol) tridecane (internal GC reference standard). The mixture was heated to reflux. After stirring the mixture at reflux for 1 h, a sample was withdrawn and quenched in a mixture of ether and 1 N HCl. GC analysis of the hydrolyzed organic phase showed the presence of 8.2 mmol of 4-(4'-methylphenyl)benzonitrile (82% chemical yield on 4-chlorobenzonitrile; identity confirmed by GC-MS) and no remaining 4-chlorobenzonitrile in the reaction mixture.

This Example illustrates the process of the instant invention wherein an unsymmetrical biaryl is prepared in high yield by reacting an arylzinc reagent with an arylchloride in the presence of a palladium catalyst. It also illustrates providing the catalyst as a palladium(II) compound. It further illustrates a catalyst comprising a bidentate chelating ligand.

Example 16

Preparation of 4-(4'-methylphenyl)benzonitrile by palladium catalyzed reaction of 4-methylphenylzinc chloride with 4-chlorobenzonitrile: The procedure was identical to Example 15, with the exception that 0.578 g (0.500 mmol) tetrakis(triphenylphosphine)palladium [Pd(PPh$_3$)$_4$] was used to provide the palladium catalyst. GC analysis of a hydrolyzed reaction sample taken after 24 h at reflux showed the presence of 2.54 mmol 4-(4'-methylphenyl)benzonitrile (25% chemical yield on 4-chlorobenzonitrile) and 6.15 mmol (62%) remaining 4-chlorobenzonitrile in the reaction mixture.

This Example illustrates the use of a palladium catalyst, provided by a palladium(0) compound, in the process of the invention.

Example 17

Preparation of 4-(4'-methylphenyl)benzonitrile by palladium catalyzed reaction of 4-methylphenylzinc chloride with 4-chlorobenzonitrile: The procedure was identical to Example 15, with the exception that 0.112 g (0.500 mmol) palladium diacetate and 0.152 g (0.500 mmol) tri-o-tolylphosphine was used to provide the ligated palladium catalyst. GC analysis of a hydrolyzed reaction sample taken after 24 h at reflux showed the presence of 4.84 mmol 4-(4'-methylphenyl)benzonitrile (48% chemical yield on 4-chlorobenzonitrile) and 0.57 mmol (5.7%) remaining 4-chlorobenzonitrile in the reaction mixture.

This Example illustrates the inventive process employing a palladium catalyst generated in situ from a palladium salt and a phosphine ligand.

Example 18

Preparation of 2-(4'-methylphenyl)benzonitrile by palladium catalyzed reaction of 4-methylphenylzinc chloride with 2-chlorobenzonitrile: The procedure was identical to Example 15, with the exception that 2-chlorobenzonitrile was reacted in place of 4-chlorobenzonitrile. GC analysis of a hydrolyzed reaction sample taken after 72 h at reflux showed the presence of 8.16 mmol of 2-(4'-methylphenyl)benzonitrile (82% chemical yield on 2-chlorobenzonitrile) and no remaining 2-chlorobenzonitrile in the reaction mixture.

This Example illustrates the process of the present invention for the preparation of 2-(4'-methylphenyl)benzonitrile by reacting a 4-methylphenylzinc reagent with 2-chlorobenzonitrile in the presence of a palladium catalyst.

Example 19

Preparation of methyl 4-(4'-methylphenyl)benzoate by palladium catalyzed reaction of 4-methylphenylzinc chloride with methyl 4-chlorobenzoate: The procedure was identical to Example 15, with the exception that 1.71 g (10.0 mmol) methyl 4-chlorobenzoate was reacted instead of 4-chlorobenzonitrile. GC analysis of a hydrolyzed reaction sample taken after 48 h at reflux showed the presence of 7.51 mmol methyl 4-(4'-methylphenyl)benzoate (75% chemical yield on methyl 4-chlorobenzoate) and 0.21 mmol (2.1%) remaining methyl 4-chlorobenzoate in the reaction mixture.

This Example illustrates the process of the present invention for palladium catalyzed reaction of an arylzinc halide reagent, derived from an arylmagnesium halide reagent, with an arylchloride bearing another functional group (ester) that can react with the arylmagnesium reagent.

Example 20

Preparation of 4-phenylbenzonitrile by palladium catalyzed reaction of diphenylzinc chloride with 4-chlorobenzonitrile: To a solution of 0.0408 g (0.0500 mmol) [1,1'-bis(diphenylphosphino)ferrocene] dichloropalladiumdichloromethane complex and 0.138 g (1.00 mmol) 4-chlorobenzonitrile in 5.0 mL of THF was added 3.42 mL (0.625 mmol) of a 0.183 M solution of diphenylzinc in THF. The mixture was heated at reflux for 4 h. GC analysis of a hydrolyzed reaction sample (using tridecane as an internal reference standard) showed the presence of 0.80 mmol 4-phenylbenzonitrile (80% chemical yield on 4-chlorobenzonitrile) and 0.021 mmol (2.1%) remaining 4-chlorobenzonitrile in the reaction mixture.

This Example illustrates the use of a diarylzinc reagent with a palladium catalyst in the process of the present invention. This Example further illustrates that both aryl groups in diarylzinc reagents can react with the arylchloride to make biaryl compounds.

Example 21

Preparation of 2-(4'-methylphenyl)benzonitrile from 4-chlorotoluene and 2-chlorobenzonitrile: A mixture of 14.6 g (600 mmol) magnesium, 63.3 g (500 mmol) 4-chlorotoluene, and 350 mL of THF was heated at reflux for 24 h. After cooling to room temperature, the stirring was stopped to allow the particulates to settle from the solution. Titration of the resulting dark, slightly cloudy solution using the method of Watson and Eastham (*J. Organomet. Chem.*, vol. 9 (1967), p. 165) gave a concentration of 1.30 M for the contained 4-methylphenylmagnesium chloride.

To 115.4 mL (150 mmol) of 1.30 M 4-methylphenylmagnesium chloride in THF was added 2.5 mL of toluene. After cooling the solution to 0° C., it was treated in one portion with 13.6 g (100 mmol) zinc chloride. The temperature of the exothermically reacting mixture was allowed to increase to ca. 45° C. The mixture was then stirred at ambient temperature for 40 minutes.

A solution containing 13.8 g (100 mmol) 2-chlorobenzonitrile, 1.93 g (7.50 mmol) nickel bis (acetylacetonate), and 2.31 mL (9.38 mmol) triisopropyl phosphite in 15 mL of THF was rapidly added to the 4-methylphenylzinc reagent mixture. The mixture was then heated to 40° C., maintained at this temperature for 135 min, then cooled to 0° C. 75 mL of 10% $H_3PO_4$ was added in portions while keeping the temperature below 25° C. With the mixture stirring vigorously at room temperature, a rapid flow of air was bubbled through the solution for 15 min to oxidize any remaining nickel(0) to nickel(II). The lower aqueous layer was separated and the remaining organic (THF) phase was extracted twice with isooctane, using 100 mL for the first extraction and 75 mL for the second (isooctane layer is on top, THF layer is on the bottom). The combined isooctane extracts were concentrated by distillation at atmospheric pressure until at least 190 mL of distillate had been collected. 110 mL of isooctane was added to the distillation pot residue and this solution was cooled to 25° C. The resultant solution (ca. 190 mL) was then washed with 25 mL of 30% aqueous methanol, and the lower phase was discarded. The stirred solution was then seeded with 5 mg of 2-(4'-methylphenyl)benzonitrile and cooled to −10° C. to effect crystallization. After crystallization had proceeded at −10° C. for 30 min, stirring was halted and the cold mother liquor was siphoned away from the settled solid. The remaining material was treated with 150 mL of isooctane and heated to 35–40° C. with stirring until all the solids had dissolved (ca. 30 min). The solution was then seeded with 5 mg of 2-(4'-methylphenyl)benzonitrile at room temperature and cooled again to −10° C. to effect crystallization. After 30 min at −10° C. the crystallized product was collected by filtration and the filter cake washed with 25 mL of cold (−10° C.) isooctane. The product was dried under reduced pressure (0.5 Torr; 25° C.) to afford 12.5 g (65%) of 2-(4-methylphenyl)benzonitrile (65% recovered yield based on 2-chlorobenzonitrile) as a fine white crystalline solid (m.p.= 50° C.; identity confirmed by $^1$H- and $^{13}$C-NMR).

This Example illustrates an entire process of the present invention for preparing 2-(4-methylphenyl)benzonitrile from 4-methylphenyl chloride (4-chlorotoluene), via the magnesium and zinc reagents, and 2-chlorobenzonitrile, including recovery of the product. This example also illustrates an arylzinc reagent prepared by reacting a zinc salt (zinc chloride) with an arylmagnesium salt (4-methylphenylmagnesium chloride) in a mole ratio in the range 1:1 to 1:2 (1:1.5) and, in principle, comprising a mixture (1:1) of the arylzinc salt and the diarylzinc compound.

Example 22

Preparation of 2-(4-methylphenyl)benzonitrile from 4-chlorotoluene and 2-chlorobenzonitrile: The reaction procedure was identical to that described in Example 21, except that the 4-methylphenylzinc reagent was prepared by reaction of 150 mmol of 4-methylphenylmagnesium chloride with 11.2 g (82.5 mmol) of zinc chloride. After the addition of the 2-chlorobenzonitrile and the nickel catalyst components, the reaction mixture was heated 40° C. for 2 h. GC analysis of a hydrolyzed reaction sample (using dodecane as an internal reference standard) showed the presence of 74.7 mmol 2-(4-methylphenyl)benzonitrile (75% chemical yield on 2chlorobenzonitrile) and 2.0 mmol (2%) remaining 2-chlorobenzonitrile.

This Example illustrates the present invention employing an arylzinc reagent prepared by reacting an a zinc salt (zinc chloride) with an arylmagnesium salt (4-methylphenylmagnesium chloride) at near a 1:2 mole ratio (1:1.8 in this Example) and, in principle, comprising predominantly a diarylzinc compound (di(4-methylphenyl) zinc).

The present invention has been shown by both description and examples. The Examples are only examples and cannot be construed to limit the scope of the invention. One of ordinary skill in the art will envision equivalents to the inventive process described by the following claims which are within the scope and spirit of the claimed invention.

We claim as our invention:

1. A process for the preparation of biaryl compounds of the formula Ar-Ar', wherein Ar and Ar' are aryl groups and may be identical or different, comprising reacting an arylzinc reagent comprising the aryl group Ar bonded to zinc with an arylchloride of the formula Ar'Cl, wherein Ar' is selected from phenyl, pyridyl, furyl, thienyl and pyrrolyl groups and substituted derivatives thereof, in the presence of a catalyst selected from the group consisting of nickel catalysts and palladium catalysts.

2. The process of claim 1 wherein the arylzinc reagent is selected from the group consisting of arylzinc salts, arylzinc compounds, or mixtures thereof.

3. The process of claim 1 wherein the arylzinc reagent is selected from the group consisting of arylzinc halides, diarylzinc compounds, or mixtures thereof.

4. The process of claim 2 wherein the arylzinc reagent is prepared by reacting a zinc salt with an arylmetal reagent selected from the group consisting of arylmagnesium reagents and aryllithium reagents.

5. The process of claim 4 wherein the arylmetal reagent is an arylmagnesium halide.

6. The process of claim 5 wherein the arylzinc reagent is prepared by reacting the zinc salt with the arylmagnesium halide in a mole ratio in the range 1:1 to 1:2.

7. The process of claim 5 wherein the arylmagnesium halide is an arylmagnesium chloride prepared by reacting an arylchloride of the formula ArCl with magnesium.

8. The process of claim 2 wherein the arylzinc reagent is prepared by reacting an arylhalide comprising the aryl group Ar with zinc.

9. The process of claim 1 wherein the catalyst is a nickel catalyst selected from the group consisting of catalysts provided by nickel(0) compounds, catalysts provided by nickel(II) compounds, and catalysts provided by nickel(II) salts.

10. The process of claim 9 wherein the catalyst comprises a ligand selected from the group consisting of monodentate, bidentate, and tridentate ligands and comprises a ligating atom selected from the group consisting of nitrogen and phosphorus.

11. The process of claim 1 wherein the catalyst is a palladium catalyst selected from the group consisting of catalysts provided by palladium(0) compounds, catalysts provided by palladium(II) compounds, and catalysts provided by palladium(II) salts.

12. The process of claim 11 wherein the catalyst comprises a ligand selected from the group consisting of monodentate, bidentate, and tridentate ligands and comprises a ligating atom selected from the group consisting of nitrogen and phosphorus.

13. A process for the preparation of 2-(4'-methylphenyl) benzonitrile comprising reacting a 4-methylphenyizinc reagent with 2-chlorobenzonitrile in the presence of a catalyst selected from the group consisting of nickel catalysts and palladium catalysts.

14. The process of claim 13 wherein the 4-methylphenylzinc reagent is prepared by reacting a zinc salt with a 4-methylphenylmagnesium reagent.

15. The process of claim 13 wherein the 4-methylphenylzinc reagent is 4-methylphenylzinc chloride prepared by reacting zinc chloride with 4-methylphenylmagnesium chloride.

16. The process of claim 15 wherein the zinc chloride is reacted with the 4-methylphenylmagnesium chloride in a mole ratio in the range 1:1 to 1:2.

17. The process of claim 13 wherein the catalyst is a nickel catalyst selected from the group consisting of catalysts provided by nickel(0) compounds, catalysts provided by nickel(II) compounds, and catalysts provided by nickel (II) salts.

18. The process of claim 17 wherein the catalyst comprises a ligand selected from the group consisting of monodentate ligands, bidentate ligands, and tridentate ligands and comprises phosphorus as a ligating atom.

19. The process of claim 18 wherein the nickel catalyst is provided by nickel bis(acetylacetonate) and comprises a trialkylphosphite ligand.

20. In a process for the preparation of biaryl compounds by reacting an arylmetal reagent with an arylhalide in the presence of a catalyst selected from the group consisting of nickel catalysts and palladium catalysts, the improvement wherein the arylmetal reagent is an arylzinc reagent and the arylhalide is an arylchloride wherein the aryl group of the arylchloride is selected from phenyl, pyridyl, furyl, thienyl and pyrrolyl groups and substituted derivatives thereof.

* * * * *